United States Patent
Gandy et al.

(10) Patent No.: US 9,511,118 B1
(45) Date of Patent: *Dec. 6, 2016

(54) PROCESS FOR REMOVING GROWTH FACTORS FROM PLATELETS

(71) Applicant: PGFX Patent Holdings. LLC, West Monroe, LA (US)

(72) Inventors: James B Gandy, West Monroe, LA (US); Robert J Brandt, Fort Myers, FL (US); Ryan N Brandt, Fort Myers, FL (US); Clark Galen, Sarasota, FL (US); Joseph Greco, Sarasota, FL (US); John Kiwczak, Sarasota, FL (US)

(73) Assignee: PGFX PATENT HOLDINGS, LLC, West Monroe, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/120,487

(22) Filed: May 23, 2014

Related U.S. Application Data

(62) Division of application No. 12/459,911, filed on Jul. 9, 2009, now Pat. No. 8,734,854.

(51) Int. Cl.
*A61K 35/14* (2015.01)
*A61K 38/18* (2006.01)

(52) U.S. Cl.
CPC .................... *A61K 38/18* (2013.01)

(58) Field of Classification Search
None
See application file for complete search history.

(56) References Cited

U.S. PATENT DOCUMENTS

| | | | |
|---|---|---|---|
| 3,375,824 A * | 4/1968 | Krakauer et al. | 604/82 |
| 4,479,896 A | 10/1984 | Antoniades | |
| 4,957,742 A | 9/1990 | Knighton | |
| 5,028,531 A | 7/1991 | Ueda et al. | |
| 5,165,928 A | 11/1992 | Smith et al. | |
| 5,733,545 A | 3/1998 | Hood, III | |
| 6,010,627 A | 1/2000 | Hood, III | |
| 6,071,267 A | 6/2000 | Zamierowski | |
| 6,214,338 B1 | 4/2001 | Antanavich et al. | |
| 6,221,575 B1 | 4/2001 | Roser et al. | |
| 6,303,112 B1 | 10/2001 | Worden | |
| 6,342,157 B1 | 1/2002 | Hood, III | |
| 6,649,072 B2 | 11/2003 | Brandt et al. | |
| 2004/0197319 A1 | 10/2004 | Harch et al. | |
| 2005/0191286 A1 | 9/2005 | Gandy | |
| 2006/0142198 A1 | 6/2006 | Gandy | |
| 2008/0213238 A1 | 9/2008 | Gandy et al. | |

FOREIGN PATENT DOCUMENTS

| | | | | |
|---|---|---|---|---|
| EP | 0308238 | * | 3/1989 | ............. A61K 37/02 |
| WO | WO 89/05656 | | 6/1989 | |
| WO | WO 95/15763 | | 6/1995 | |
| WO | WO 2007/005912 | | 1/2007 | |

OTHER PUBLICATIONS

Richter et al. "Composition of the peptide fraction in human blood plasma: database of circulating human peptides" Journal of Chromatography B, 726 (1999) 25-35.*

* cited by examiner

*Primary Examiner* — Thane Underdahl
(74) *Attorney, Agent, or Firm* — Price & Adams, P.C.

(57) ABSTRACT

A sub-atmospheric, negative pressure is applied to a growth factor starting material, such as whole blood, to release growth factors and plasma in a non-destructive medium. The released growth factors having a weight of about 70-76 kDaltons are applied in either a filtered or unfiltered state to a wound to promote healing of the wound. The released growth factors are applied topically to the area of a surface wound to effect healing. The released growth factors are also injected into soft tissue, such as a torn tendon, to promote tissue growth and healing. The growth factors are released in one method from a patient's own blood. In another method the growth factors are released from a whole blood source and freeze dried by conventional lyophilization. Then at a later date, the freeze dried product is reconstituted by normal saline for treatment of a patient's wound or for use in a surgical procedure.

17 Claims, No Drawings

PROCESS FOR REMOVING GROWTH FACTORS FROM PLATELETS

CROSS-REFERENCE TO RELATED APPLICATION

This application is a division of U.S. application Ser. No. 12/459,911 filed on Jul. 9, 2009.

BACKGROUND OF THE INVENTION

1. Field of the Invention

The invention relates to a process for extracting and isolating growth factors from platelets and, more particularly, to a wound healing composition of growth factors released from mammalian platelet membranes for use in wound healing and other therapeutic uses.

2. Description of the Prior Art

The wound healing process is generally considered to occur in several stages, generally known as the healing cascade. After tissue injury, platelets are among the first cells to appear in the vicinity of the wound. Activation of a platelet by an agonist, such as thrombin, or other agonists known in the art, leads to the release of granule material from within the platelet. Such granulation activation results in the release of proteins known as growth factors, primarily concentrated in the alpha granules of platelets. Released growth factors stimulate the formation of new tissue.

When applied to wounds, growth factors are known to increase the rate of collagen laydown, vascular ingrowth, fibroblast proliferation and overall healing. The release of a protein known as platelet-derived growth factor (PDGF) is a chemotactic signal for monocytes, neutrophils and fibroblasts which then move into the wound to begin the inflammatory stage of the healing process. During this time, monocytes secrete a number of factors, including PDGF and transforming growth factor-beta 1 (TGF-$\beta$1) (also found in platelets). In this manner fibroblasts are activated to begin the repair stage of the healing process. Subsequently, wound healing continues through the process of collagen remodeling within the wound.

It is known to use activated autologous platelets as a treatment in a number of medical and surgical procedures, including but not limited to oral and maxillofacial surgery, orthopedic surgery, cosmetic and reconstructive surgery, chronic tissue repair, sports medicine injuries, neurosurgery, cardiovascular surgery, podiatry, hair transplant surgery, medical research, tissue engineering, and non-surgical cellular therapy. U.S. Pat. Nos. 4,957,742 and 6,649,072 disclose wound healing compositions that include platelet enriched plasma which prior to use is activated by thrombin to release growth factors from the alpha granules of the platelets.

Extracting therapeutic levels of platelets has been a technical challenge requiring trained cardiovascular perfusionists to operate the equipment originally designed for the production of platelet rich plasma (PRP). The clinical practitioner now has access to more simplified equipment that allows him to process PRP with smaller amounts of whole blood in a shorter amount of time. Venous access, clinical expertise, and cost are still challenges that have limited the widespread use of this process throughout the world. Moreover from a commercial standpoint, wound healing compositions that include platelets must meet costly FDA guidelines applicable to blood products.

Growth factors are responsible for the wound healing process, as described above. Platelets function merely as carriers for the growth factors. Therefore, there is a need for an inexpensive and efficient process for extracting and isolating growth factors from the platelets contained in plasma for subsequent use in wound healing. The final product preferably may be free of other components that are typically found in conventional platelet enriched wound healing products, namely the platelets themselves, ghost platelets, white blood cells, red blood cells, bacteria, and other cellular debris.

It is further desirable to prepare a wound healing product that can be subjected to conventional preservations, such as lyophilization, freeze drying, and cryopreservation in a process that does not destroy the growth factors. In this manner the shelf life of the product would be prolonged.

Therefore, there is a need for a process for isolating and extracting growth factors in a non-destructive manner from platelets. The resulting composition may or may not be substantially free of other components, such as platelets, ghost platelets, white blood cells, red blood cells and bacteria, and can be used immediately fresh or lyophilized or freeze dried into a shelf-stable product for subsequent use.

SUMMARY OF THE INVENTION

In accordance with the present invention, there is provided a wound healing composition that includes a growth factor starting material containing platelets. The growth factor starting material is subjected to a preselected negative pressure. The growth factors are released from the growth factor starting material by the negative pressure.

Further in accordance with the present invention there is provided a wound healing composition prepared by a process that includes the step of applying a vacuum force of a preselected magnitude to a growth factor starting material at room temperature. Growth factors are released from the growth factor starting material by the vacuum force. The released growth factors are provided in a bioactive state.

Further in accordance with the present invention there is provided a therapeutic plasma composition prepared by a process that includes the step of providing a growth factor starting material containing platelets. The growth factor starting material is subjected to a preselected negative pressure to release growth factors therein. The growth factors are separated from the growth factor starting material to form a plasma composition for therapeutic use that is substantially free of growth factors.

Accordingly, a principal object of the present invention is to provide a process for releasing growth factors from growth factor starting material for use in wound healing medical procedures.

Another object of the present invention is to provide a process that separates growth factors from platelets and preserves the growth factors in a concentration for improved wound healing.

Another object of the present invention is to provide a wound healing composition that includes growth factors released from a starting material in a bioactive state for enhancing tissue growth.

A further object of the present invention is to provide a process for releasing growth factors by negative pressure from platelets in plasma at room temperature and preserving the growth factors by lyophilization for future use in wound treatment.

These and other objects of the present invention will be more completely disclosed and described in the following specification and appended claims.

DESCRIPTION OF THE PREFERRED EMBODIMENTS

The process of the present invention removes growth factors from platelets for subsequent use in wound healing, either alone or in combination with other wound healing components. With known prior art methods, platelet concentrated plasma products are prepared through multistep processes and then subsequently activated with thrombin or collagen prior to use to release the growth factors from the platelets' alpha granules. In contrast, the process of the present invention allows for the separation of growth factors from concentrated platelets without the need to use thrombin for activation. Consequently, less steps are required to isolate the growth factors. After the separation process, the growth factors are released in a bioactive state in a nondestructive medium, such as plasma, sterile water, saline, and the and the like. In a bioactive state the released growth factors have a positive reaction on living tissue, which in one example provides enhanced wound healing. The growth factors may be lyophilized, for example, to prepare a freeze-dried product with a shelf life much longer than non-lyophilized platelet products.

As used herein, growth factor refers to any material or materials having a positive reaction on living tissues, such as promoting the growth of tissues. Exemplary growth factors include, but are not limited to, platelet-derived growth factor (PDGF), platelet-derived angiogenesis factor (PDAF), vascular endotheial growth factor (VEGF), platelet-derived epidermal growth factor (PDEGF), platelet factor 4 (PF-4), transforming growth factor beta. (TGF-B), acidic fibroblast growth factor (FGF-A), basic fibroblast growth factor (FGF-B), transforming growth factor A (TGF-A), insulin-like growth factors 1 and 2 (IGF-1 and IGF-2), B thromboglobulin-related proteins (BTG), thrombospondin (TSP), fibronectin, von Wallinbrand's factor (vWF), fibropeptide A, fibrinogen, albumin, plasminogen activator inhibitor 1 (PAI-1), osteonectin, regulated upon activation normal T cell expressed and presumably secreted (RANTES), gro-A, vitronectin, fibrin D-dimer, factor V, antithrombin III, immunoglobulin-G (IgG), immunoglobulin-M (IgM), immunoglobulin-A (IgA), a2-macroglobulin, angiogenin, Fg-D, elastase, keratinocyte growth factor (KGF), epidermal growth factor (EGF), fibroblast growth factor (FGF), tumor necrosis factor (TNF), fibroblast growth factor (FGF) and interleukin-1 (IL-1), Keratinocyte Growth Factor-2 (KGF-2), and combinations thereof. One of the important characteristics common to the above listed growth factors is that each substance is known or believed to have a positive reaction on living tissue, known as bioactivity, to enhance cell or tissue growth.

It should be understood herein that growth factor starting materials include, but are not limited to, platelets, platelet rich plasma, whole blood, bone marrow, umbilical cord fluid and combinations thereof. For improved clinical use of growth factors, it is important that the growth factor starting material not be frozen prior to separation of the growth factors from platelets. Preferably, the process should be performed above freezing temperatures, preferably room temperature. In the preferred embodiment of the present invention, platelet rich plasma (PRP) is employed as the source of the growth factors and may be obtained via methods known in the art.

Exemplary platelet plasma products are disclosed in U.S. Pat. Nos. 6,214,338; 6,010,627; 5,165,928; 6,303,112; 6,649,072. The more concentrated the plasma is with platelets, the greater the concentration of growth factors that can be obtained via the present invention. The process for isolating growth factors from platelet rich plasma or other media containing platelet rich plasma is described hereinafter in greater detail.

As used herein, therapeutically effective amount refers to the amount or amounts of the constituent bioactive elements or combination thereof necessary to enhance wound healing. Examples of wound healing include the reduction in the volume or surface area of a wound, the increase in the amount of granulation tissue or other biological material facilitating collagen laydown, vascular ingrowth, fibroblast proliferation or overall healing. All embodiments of the present invention are assumed to have the therapeutically effective amount(s) of constituent substances or combinations thereof to possess the above positive bioactive properties.

Once the platelet rich plasma (PRP) is obtained, it is placed under a vacuum, preferably under a sub-atmospheric or negative pressure. The PRP is in an unfrozen state, preferably at room temperature. Similarly, the vacuum is applied at above freezing, more preferably at room temperature conditions.

In accordance with the present invention, the PRP is placed in one or more vials. A vacuum is applied using a conventional vacuum pump, wherein the platelet rich plasma product is placed in a separate vacuum chamber. The vacuum pump is operated to apply a negative pressure to the PRP. The vacuum is applied preferably at temperatures above freezing. In one example, it is applied between 1° C. and 37° C. and at a sub-atmospheric, negative pressure preferably between 5 millibars and 1 atmosphere. As a result of the application of the negative pressure, the growth factors are released into the surrounding nondestructive medium.

There is a direct inverted correlation between time versus vacuum pressure. The shorter the length of time the vacuum is applied, the higher the vacuum pressure must be. Conversely, the longer the length of time the vacuum is applied, the lower the vacuum pressure needs to be to release the growth factors form the platelets. A vacuum source suitable for use in the process of the present invention is a rotary vane direct drive vacuum pump commercially available from Labconco Corporation of Kansas City, Mo. It should be understood that other commercially available vacuum generating devices are operable for use in the present invention.

As a result of the vacuum process, the growth factors are separated or released from the platelets in the growth factor starting material into the plasma, leaving the platelets intact. The negative pressure created by the vacuum pulls the growth factors out of the platelets and into the plasma. The separated growth factors are mixed with a medium that is not destructive to the growth factors in a bioactive state to promote tissue growth. The platelets also remain for therapeutic use. In one example of the process of the present invention, analysis of the vacuumed plasma using light microscopy and alpha granule staining techniques revealed intact platelets devoid of alpha granules in addition to the presence of platelet derived growth factors (PDGF) distributed in the plasma. Platelet derived growth factors typically have a weight of 16-20 kDaltons. The growth factors extracted from the platelets in accordance with the present invention were measured to have an increased weight of 70-76 kDaltons.

In another example, the process of the present invention for isolating growth factors is conducted using a composition of platelet rich plasma (PRP) and platelet poor plasma (PPP), as described in U.S. Pat. No. 6,649,072 (hereinafter referred to as the '072 patent. The composition disclosed in the '072 patent is a 3:1 ratio of PRP to PPP. With this ratio of PRP to PPP, the amount of growth factors obtained is platelet derived growth factor-AB/BB 356673.86 pg/ml, vascular endothelial growth factor 6440.667 pg/ml and platelet-derived epidermal growth factor 1106.73 pg/ml. This constitutes a significant recovery of growth factors not otherwise attainable for positive clinical use in applying topically to a wound or injecting into soft tissue, such as a tendon.

In another embodiment of the present invention, the growth factors are preserved for future bioactive use by preservation methods, such as lyophilization, freeze drying and cryopreservation. For example, the resulting vacuumed plasma product comprising growth factors and empty platelets are preserved via conventional methods, such as lyophilization, freeze drying and cryopreservation. In this manner a shelf-stable product is produced that is usable for several days or even months to years after preparation. When desired for use, the freeze-dried product is reconstituted with sterile 0.9% normal saline solution.

The vacuumed product, as above described, contains growth factors and platelets. The vacuumed product may be used immediately or lyophilized or freeze dried for future use. In accordance with another embodiment of the present invention, the vacuumed product is filtered using a 0.2 micron filter. The filtered composition contains growth factors substantially free of platelets, ghost platelets, bacteria, red blood cells, white blood cells, and cellular debris.

A preferred filter is one having a porosity of 0.2 microns or less. By filtering the vacuumed product, the released growth factors are free of cellular debris, platelet membranes, ghost platelets, white blood cells, bacteria, and red blood cells.

Growth factors preserved as above described are reconstituted or hydrated in one method using sterile 0.9% normal saline solution. The preserved product is also reconstituted using deionized water, sterile water, other liquid media or bodily fluids including, but not limited to, plasma, hemoconcentrated plasma, whole blood, bone marrow aspirate, antibiotics or any combination thereof.

In another example of the present invention, 3 milliliters of the preserved product containing about 70% growth factors is reconstituted with about 3 milliliters of 0.9% normal saline or similar liquid media, as discussed above. For wound healing purposes, a therapeutically effective amount of the reconstituted product is applied topically to cover the wound. It may also be injected at a location of soft tissue injury. Beyond wound healing, the fresh product and reconstituted product is useful in medical research applications, such as culturing out stem cells. The reconstituted product may also be a liquid product containing protein-bound growth factors not previously lyophilized.

Prior to preserving the isolated growth factors, in another process various pharmaceutical agents are added to the composition. Preferably, these agents aid in the bioactivity of wound healing and in the treatment/prevention of infection. The agents include antibiotics, antifungal agents, and the like. However, as known in the art, any number of other pharmaceutical agents may be employed. The quantity and type of agent selected must be stable in such products and be capable of withstanding lyophilization and other methods of preserving the wound healing product of the present invention.

In a further embodiment of the present invention, a bodily fluid, such as blood or an antibiotic, is used to reconstitute the final preserved product. This final product allows the clinician a wide berth of options on how it is used. In another example, a practitioner adds bone marrow aspirate and stem cells to the final product so that the patient will achieve benefits from both therapies. Additionally, a practitioner can administer the final product with an antibiotic solution at a specific anatomical site for wound healing and the like. Further, the lyophilized final product and a thrombin solution are combined to initiate a clot to be placed in a desired location to promote tissue growth.

The process of the present invention is a significant advancement in the field of using platelet based wound therapy agents. The process allows for the simple preparation of a product having growth factors that may be subsequently lyophilized or preserved for bioactive use at a later date. The growth factors produced by the process of the present invention have demonstrated positive clinical signs in closing wounds and healing damaged soft tissue. In this manner large scale production of shelf-ready wound healing products is facilitated.

This invention will be further understood by reference to the following examples, which should not be construed to limit the invention.

EXAMPLE 1

A wound healing composition was prepared by drawing a quantity of whole blood from a patient having a surface wound via conventional practice. The whole blood was collected in a vial. The vial was placed in a conventional blood separation-type centrifuge and spun at a preselected speed for a time interval to separate the platelet rich plasma from the platelet poor plasma. The platelet rich plasma was extracted from the vial and placed in a container. At room temperature, the container of platelet rich plasma was placed in an airtight chamber. A pressure below atmospheric pressure was applied to the chamber by a vacuum pump supplied by Labconco Corporation. The sub-atmospheric pressure separated the growth factors from the platelets in the plasma. The separated growth factors were found to have a weight in the range of 70-76 kDaltons. The separated growth factors were applied topically to the area of a surface wound of the patient, and the wound healing was enhanced.

EXAMPLE 2

A wound healing composition was prepared by drawing a quantity of whole blood from a patient having a soft tissue wound in a tendon in accordance with Example 1 above. The whole blood was then separated into three distinct components using a centrifuge in accordance with the method disclosed in U.S. Pat. No. 6,649,072. The separated components of platelet rich plasma and the platelet poor plasma were combined to provide a growth factor starting material. The growth factor starting material was then subjected to negative pressure using a vacuum pump as set forth in Example 1 above. Growth factors were released from the starting material and maintained in the surrounding nondestructive medium. The released growth factors were then conveyed through a 0.2 micron filter. The filtered growth factors were found to be free of platelets, ghost platelets, bacteria, red blood cells, white blood cells and cellular debris. The filtered growth factors were then injected into a soft tissue wound of the patient. The injection was found to enhance healing of the wound.

EXAMPLE 3

A wound healing composition was prepared from a healthy individual not having a wound by drawing a quantity of whole blood in accordance with Example 1 above. Growth factors were released from the whole blood by performing the method steps described in Example 2 above. A first quantity of the released growth factors were filtered in the manner also described in Example 2. A second quantity of the released growth factors were not filtered. The filtered and unfiltered growth factors were lyophilized in a conventional manner to provide a preserved, shelf-stable product. After a preselected period of time after lyophilization the two quantities of preserved growth factors were reconstituted or hydrated by mixing the preserved growth factors with a sterile 0.9% normal saline solution. One quantity of the reconstituted growth factors was applied topically to the area of a surface wound of one patient. The second quantity of the reconstituted growth factors was injected into a soft tissue wound of a second patient. In each patient the wound healing took place in an enhanced manner.

According to the provisions of the patent statutes, we have explained the principle, preferred construction and mode of operation of our invention and have illustrated and described what we now consider to represent its best embodiments. However, it should be understood that, within the scope of the appended claims, the invention may be practiced otherwise than as specifically illustrated and described.

We claim:

1. A wound healing composition comprising:
    a growth factor starting material containing platelets,
    said growth factor starting material subjected to a preselected negative pressure,
    growth factors being released from said growth factor starting material by the negative pressure to separate the growth factors from the growth factor starting material without activating the platelets in the growth factor starting material, and
    said separated growth factors mixed with plasma for application to a wound to promote tissue growth.

2. A wound healing composition as set forth in claim 1 which includes:
    a pharmaceutical agent added to said mixture of said nondestructive medium and said growth factors released from said platelets for application in wound treatment.

3. A wound healing composition as set forth in claim 1 which includes:
    said growth factor starting material selected from the group consisting of platelets, platelet rich plasma, blood, bone marrow, umbilical cord fluid, and combinations thereof.

4. A wound healing composition as set forth in claim 1 in which:
    said growth factor starting material includes a combination of platelet rich plasma and platelet poor plasma.

5. A wound healing composition as set forth in claim 1 which includes:
    said released growth factors being filtered to remove other components in said growth factor starting material from said released growth factors.

6. A wound healing composition as set forth in claim 1 which includes:
    said released growth factors being lyophilized.

7. A wound healing composition prepared by a process comprising the steps of:
    applying a vacuum force of a preselected magnitude to a growth factor starting material containing platelets at room temperature,
    releasing growth factors from the growth factor starting material by the vacuum force to separate the growth factors from the growth factor starting material without activating the platelets in the growth factor starting material, and
    mixing the separated growth factors in a bioactive state with plasma.

8. A wound healing composition as set forth in claim 7 which includes:
    releasing the growth factors from the growth factor starting material selected from the group consisting of platelets, platelet rich plasma, blood, bone marrow, umbilical cord fluid, and combination thereof.

9. A wound healing composition as set forth in claim 7 which includes:
    releasing the growth factors from the growth factor starting material including a combination of platelet rich plasma and platelet poor plasma.

10. A wound healing composition as set forth in claim 7 which includes,
    filtering the released growth factors from other components within the growth factor starting material.

11. A wound healing composition as set forth in claim 7 which includes,
    freeze drying the released growth factors to provide a self-stable product.

12. A wound healing composition as set forth in claim 11 which includes:
    mixing the shelf-stable product with a preselected material to reconstitute the freeze dried growth factors for therapeutic application.

13. A therapeutic plasma composition prepared by a process comprising the steps of:
    selecting a growth factor starting material containing platelets,
    subjecting the growth factor starting material to a preselected negative pressure to release growth factors therein without activating the platelets,
    separating the growth factors from the growth factor starting material, and
    mixing the separated growth factors with plasma to form a plasma composition in a therapeutically effective amount to provide wound healing.

14. A therapeutic plasma composition as set forth in claim 13 in which the process includes:
    releasing the growth factors from the platelets in the growth factor starting material.

15. A therapeutic plasma composition as set forth in claim 13 in which the process includes:
    releasing the growth factors from the growth factor starting material selected from the group consisting of platelets, platelet rich plasma, blood, bone marrow, umbilical cord fluid, and combinations thereof.

16. A therapeutic plasma composition as set forth in claim 13 in which the process includes:
    releasing the growth factors from the growth factor starting material having a combination of platelet rich plasma and platelet poor plasma.

17. A therapeutic plasma composition as set forth in claim 13 in which the process includes:
    filtering the released growth factors from the growth factor starting material to form the plasma composition for therapeutic use.

* * * * *